United States Patent
Weidinger

(10) Patent No.: US 12,328,052 B2
(45) Date of Patent: Jun. 10, 2025

(54) GANTRY DRIVE WITH INTEGRAL POWER TRANSMISSION

(71) Applicant: Siemens Healthineers AG, Forchheim (DE)

(72) Inventor: Thomas Weidinger, Erlangen (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 183 days.

(21) Appl. No.: 18/325,286

(22) Filed: May 30, 2023

(65) Prior Publication Data
US 2023/0387744 A1    Nov. 30, 2023

(30) Foreign Application Priority Data
May 31, 2022 (EP) .................................... 22176539

(51) Int. Cl.
| | |
|---|---|
| *H02K 5/00* | (2006.01) |
| *H02K 1/12* | (2006.01) |
| *H02K 1/22* | (2006.01) |
| *H02K 11/30* | (2016.01) |

(52) U.S. Cl.
CPC ............ *H02K 5/00* (2013.01); *H02K 1/12* (2013.01); *H02K 1/22* (2013.01); *H02K 11/30* (2016.01)

(58) Field of Classification Search
CPC .. H02K 1/12; H02K 1/22; H02K 5/00; H02K 11/30
USPC ........................................................ 310/68 R
See application file for complete search history.

(56) References Cited

U.S. PATENT DOCUMENTS

| | | | |
|---|---|---|---|
| 2002/0031201 A1 | 3/2002 | Suzuki et al. | |
| 2014/0275953 A1* | 9/2014 | Gregerson | A61B 6/035 600/407 |
| 2015/0085969 A1* | 3/2015 | Mekonnen | H05G 1/10 378/4 |
| 2016/0220216 A1* | 8/2016 | Karahashi | A61B 6/5288 |
| 2016/0287197 A1* | 10/2016 | Risher-Kelly | H02P 9/06 |
| 2017/0007197 A1 | 1/2017 | Beyerlein et al. | |
| 2017/0025890 A1* | 1/2017 | Splinter | H05G 1/10 |
| 2017/0214279 A1* | 7/2017 | Smith | H02K 1/12 |
| 2018/0085085 A1* | 3/2018 | Hannemann | G01B 7/30 |
| 2023/0284988 A1* | 9/2023 | Maji | A61B 6/4482 |
| 2023/0387744 A1* | 11/2023 | Weidinger | A61B 6/56 |
| 2024/0207649 A1* | 6/2024 | Wiberg | A61N 5/1081 |

(Continued)

FOREIGN PATENT DOCUMENTS

| | | |
|---|---|---|
| DE | 102014201805 A1 | 8/2015 |
| EP | 0181176 A2 | 5/1986 |
| JP | 2004202092 A | 7/2004 |

*Primary Examiner* — Rashad H Johnson
(74) *Attorney, Agent, or Firm* — Harness, Dickey & Pierce, P.L.C.

(57) ABSTRACT

A gantry drive includes a multiphase stator, a multiphase rotor, a tunnel-shaped cavity configured to receive a patient, and a controller. The multiphase rotor spatially surrounds the cavity. The multiphase stator and the multiphase rotor form a multiphase motor configured to produce a rotating-field power. A first portion of the rotating-field power provides a mechanical drive power to produce a rotational movement of the multiphase rotor, and a second portion of the rotating-field power provides an electrical supply power for a payload apparatus. The controller is configured to vary at least one of the first portion or the second portion.

20 Claims, 6 Drawing Sheets

(56) References Cited

U.S. PATENT DOCUMENTS

2025/0032058 A1\* 1/2025 Simsekli ................ A61B 6/03
2025/0032200 A1\* 1/2025 Hofstetter ............. A61B 34/30

\* cited by examiner

GANTRY DRIVE WITH INTEGRAL POWER TRANSMISSION

CROSS-REFERENCE TO RELATED APPLICATION(S)

The present application claims priority under 35 U.S.C. § 119 to European Patent Application No. 22176539.9, filed May 31, 2022, the entire contents of which are incorporated herein by reference.

FIELD

One or more example embodiments of the present invention relate to a gantry drive, to a computed tomography apparatus, to a method for producing a rotational movement of a multiphase rotor via a gantry drive, to an associated non-transitory computer-readable storage medium and/or an associated non-transitory computer program product.

BACKGROUND

A conventional gantry for a computed tomography apparatus typically has two carrier rings mounted around a tunnel-shaped cavity. The two carrier rings are usually mounted for rotation relative to one another, so that one of the two carrier rings forms a stationary carrier ring and the other of the two carrier rings forms a rotating carrier ring.

If an X-ray source and an X-ray detector are mounted on the rotating carrier ring, the rotating carrier ring is usually rotated in a rotational movement around the cavity by typically at least one half revolution, in particular by a multiplicity of revolutions. A mechanical drive power is needed to perform the rotational movement.

During the rotational movement, X-rays produced by the X-ray source are used to X-ray, for example, a patient arranged in the cavity (or an object arranged in this way), and attenuation profiles dependent on the X-rayed patient can be detected by the X-ray detector and used to reconstruct a tomographic image. A conventional X-ray source or X-ray detector of this type is a payload, which is supplied on the rotating carrier ring with electrical power during operation.

A conventional gantry therefore typically has two mutually separate power transmission systems, in particular one system for providing the mechanical drive power and a further system for transmission of the electrical supply power. A large number of variants of conventional gantry drives of this type are fundamentally known for transmission of the mechanical drive power used for the rotational movement of the rotating carrier ring. In particular, the conventional gantry drive can be a direct drive. The conventional direct drive can be embodied, for example, as a permanently excited synchronous motor, in which magnets are mounted on the rotating part, and thus power for the direct drive is provided solely on the stationary part. Alternatively, the conventional gantry can be driven via gears and/or a belt. Examples here are gear couplings, V-belt drives, etc.

In general, the transmission of the electrical supply power can be contactless or contact-based. Contact-based transmission mechanisms typically comprise an arrangement of a brush and a slip ring, which are in contact with each other and can rotate, and in which the electrical supply power can be transmitted as a DC or AC voltage between the stationary carrier ring and the rotating carrier ring. Contactless power transmission is normally performed via windings which are inserted in magnetic cores and operated with an AC voltage, and which are arranged opposite each other, one on the stationary carrier ring and one on the rotating carrier ring in each case. Different variants relating thereto from the prior art are also known to a person skilled in the art.

In addition, a conventional gantry can comprise a data transmission system for transmitting data, in particular the detected attenuation profiles. Such a data transmission system can comprise a capacitive, resistive, inductive or optical transmitter and/or receiver.

The conventional gantry drive is typically designed to be able to produce in an acceleration stage a rotational movement of the rotating carrier ring. Especially when accelerating from a standstill, a large amount of mechanical drive power is needed compared with a later point in time at which the target speed of the rotating carrier ring is reached. A conventional gantry drive accordingly keeps power in reserve, which is called upon in particular in the acceleration stage, but is needed to a lesser degree in a continuation stage, which follows the acceleration stage.

At the same time, the system needs a significant amount of installation space for the transmission of the electrical supply power. A certain degree of maintenance effort or wear arises depending on the configuration of the transmission mechanism, for instance caused by the friction between brush and slip ring.

SUMMARY

An object of one or more embodiments of the present invention is to define a gantry drive, a computed tomography apparatus, a method for producing a rotational movement of a multiphase rotor via a gantry drive, and an associated non-transitory computer-readable storage medium and/or non-transitory computer program product, for which less installation space is needed.

At least this object is achieved by the features of the independent claims and embodiments described herein. Advantageous embodiments are described in the dependent claims.

The gantry drive, according to an embodiment of the present invention, has:
 a multiphase stator;
 a multiphase rotor;
 a tunnel-shaped cavity for receiving a patient; and
 a control unit,
 wherein the multiphase rotor spatially surrounds the cavity,
 wherein the multiphase stator and the multiphase rotor form a multiphase motor for providing a rotating-field power,
 wherein via the rotating-field power, in the form of a first portion, can be provided a mechanical drive power for producing a rotational movement of the multiphase rotor, and, in the form of a second portion, can be provided an electrical supply power for a payload apparatus,
 wherein the control unit is designed to vary the first portion and/or the second portion.

The gantry drive, according to an embodiment of the present invention, has:
 a multiphase stator;
 a multiphase rotor;
 a tunnel-shaped cavity configured to receive a patient; and
 a controller,
 wherein the multiphase rotor spatially surrounds the cavity, wherein the multiphase stator and the multiphase rotor form a multiphase motor to provide a rotating-field power, wherein a first portion of the rotating-field power provides a mechanical drive power to produce a rotational movement of the multiphase rotor, and a second portion of the rotating-field power provides an electrical supply power for a payload apparatus, wherein the controller is configured to vary the first portion and/or the second portion.

The method, according to an embodiment of the present invention, for producing the rotational movement of the multiphase rotor of the gantry drive comprises the following steps:

providing the rotating-field power in the multiphase motor in such a way that a first portion of the rotating-field power acts as a mechanical drive power for producing the rotational movement of the multiphase rotor of the multiphase motor, and a second portion of the rotating-field power acts as the electrical supply power for the payload apparatus. In other words, the rotating-field power in the multiphase motor is provided in particular in such a way that the rotating-field power, in the form of the first portion, provides the mechanical drive power for producing the rotational movement of the multiphase rotor of the multiphase motor, and, in the form of the second portion, provides the electrical supply power for the payload apparatus. The provided rotating-field power can be used in particular to drive the multiphase motor with the mechanical drive power and to operate the payload apparatus with the electrical supply power.

The non-transitory computer-readable storage medium and/or non-transitory computer program product, according to an embodiment of the present invention, has program instructions, which can be loaded directly into a memory of the processing unit of the control unit of the gantry drive, in order to perform the method when the program instructions are executed in the processing unit.

The gantry drive, or the use of said gantry drive, in particular has the advantage that separate systems do not have to be provided for mechanical and electrical power transmission. In other words, in particular there is no need for the separate contactless or contact-based power transmission mechanism because the electrical supply power can be provided via the gantry drive. In the gantry drive is integrated in particular a contactless power transmission mechanism. In other words, the gantry drive acts additionally as a contactless power transmission mechanism. This typically saves installation space.

Preferably, in particular in the gantry drive, according to an embodiment of the present invention, power held in reserve for the acceleration stage is better utilized also after the acceleration stage. In particular, the total power of the direct drive can be increased as a result of the saving in installation space, which leads advantageously to faster acceleration of the multiphase rotor and/or to a higher maximum value of the electrical supply power. An acceleration time compared with a conventional gantry drive can be reduced advantageously by a factor of 2, particularly advantageously by a factor of 4 to 6. The acceleration time of the gantry drive, according to an embodiment of the present invention, equals in particular less than 30 s, preferably less than 10 s, particularly advantageously less than 5 s. Preferably, without brush and slip ring, there is less or no maintenance effort.

The gantry drive is in particular a drive for driving a gantry. In particular, the gantry drive is a direct drive. The multiphase rotor is driven in particular directly by the multiphase stator. In particular, the gantry is configured for a computed tomography apparatus. The gantry drive has a mechanical drive power such that the rotational movement through 360°, which corresponds to one period of rotation, is performed in less than 2 s, typically less than 1 s, preferably less than 0.5 s. In other words, the mechanical drive power is so high that the period of rotation can approach 0.2 s. The mechanical drive power can preferably be so high that a g-force at the periphery during operation of the gantry exceeds 10 g, 20 g and/or 50 g.

The tunnel-shaped cavity is usually a central opening in the gantry drive. A diameter of the cavity is typically greater than 10 cm and/or less than 150 cm. A rotational axis of the multiphase rotor typically corresponds to a center axis of the tunnel-shaped cavity. It is conceivable in principle that in addition, the multiphase stator spatially surrounds the cavity. In particular, the patient can be placed in the tunnel-shaped cavity. Alternatively, instead of a patient, an object under examination, for instance for materials testing, can be located in the tunnel-shaped cavity.

The multiphase stator and the multiphase rotor form the multiphase motor, i.e. an electrical machine. The multiphase motor can have, in addition to the multiphase stator and the multiphase rotor, at least one further component, which is designed to provide jointly with the multiphase stator and the multiphase rotor the rotating-field power. Usually the multiphase motor does not consist solely of the multiphase stator and the multiphase rotor. In other words, the multiphase stator and the multiphase rotor are essential, but not the only, components of a multiphase motor.

The providing of the rotating-field power comprises in particular producing the rotating-field power and/or taking-up the rotating-field power. The providing of the rotating-field power comprises in particular producing a rotating field that is typically suitable for performing work on a unit that takes up the rotating-field power. The providing of the rotating-field power preferably facilitates the transmission of the mechanical drive power and of the electrical supply power.

In particular, the multiphase motor has a symmetrical design. This means that the rotating-field power can be transmitted back and forth in particular between the multiphase stator and the multiphase rotor. In other words, the multiphase stator can be designed to produce the rotating-field power, and the multiphase rotor to take up the rotating-field power. Alternatively or additionally, the multiphase rotor can be designed to produce the rotating-field power, and the multiphase stator to take up the rotating-field power. Depending on the configuration of the gantry drive, the rotating-field power can be provided by the multiphase stator and the multiphase rotor.

On the stator side, the input power for the multiphase motor can be provided, for example, by a mains supply and/or by an energy buffer. The normal operating mode of the gantry drive is in particular mains operation, when the input power is provided by the mains supply. On the rotor side, the input power for the multiphase motor can be provided typically by an energy buffer. Operating the gantry drive in this way can be called in particular UPS operation. The operation of the multiphase motor, in particular of the multiphase stator and/or of the multiphase rotor, is typically lossy. The magnitude of the rotating-field power produced is typically less than the magnitude of the input power.

The multiphase motor in particular has the drive principle of an asynchronous machine and/or is an asynchronous machine. In particular, the multiphase motor is an asynchronous motor. The multiphase windings form in particular three-phase motor windings. The multiphase motor is usually designed to have three phases. In principle, another number of phases is possible, for instance two phases or more than three phases, in particular six phases. The terms used in the present application, in particular those that comprise the prefix "multiphase", for example the terms multiphase motor, multiphase stator, multiphase rotor, multiphase winding, typically include the associated operation with three phases and also the associated operation with a number of phases not equal to three.

The multiphase motor, in particular the multiphase windings, can have a drum-shaped or disc-shaped alignment. The drum-shaped alignment is known to mean that the rotating-field power is transmitted substantially in a radial direction, whereas in the case of the disc-shaped alignment, the rotating-field power is transmitted substantially in an axial direction.

The providing of the mechanical drive power in particular drives the multiphase rotor relative to the multiphase stator. Depending on the choice of reference system, the multiphase rotor can move relative to the multiphase stator, or vice versa. The multiphase rotor can be driven in particular by the mechanical drive power provided, with the multiphase rotor typically performing a rotational movement. The rotational movement is in particular a relative movement. The providing of the electrical supply power in particular operates the payload apparatus. The payload apparatus can be operated, or is operating, in particular by the electrical supply power provided.

The multiphase stator in particular has multiple poles and/or has at least one multiphase winding, which is typically mounted in, or around, a stator yoke. The stator yoke comprises iron for example. The multiphase stator preferably has at least one multiphase winding for each of the three phases of a mains supply, with the connection of the multiphase stator to the mains supply usually being made via a stationary converter. The multiphase stator typically uses an input power, in particular an electrical input power, for producing the rotating-field power, in particular in mains operation.

In operation, the multiphase rotor takes up in particular the rotating-field power. The taking-up of the rotating-field power facilitates in particular the providing of the mechanical drive power and the electrical supply power. The rotating-field power is taken up typically across an air gap between the multiphase stator and the multiphase rotor. The rotating-field power is taken up in particular in a contactless manner. The availability of the mechanical drive power and/or of the electrical supply power depends in particular on the availability of the rotating-field power.

The multiphase rotor typically has the same number of poles as the multiphase stator, and/or has at least one multiphase winding, which is typically mounted in, or around, a rotor yoke. The rotor yoke comprises iron for example. The multiphase rotor preferably has at least one multiphase winding for each of the three phases of the mains supply.

The gantry drive is configured in particular to provide, via the rotating-field power, in the form of the first portion, the mechanical drive power for producing the rotational movement of the multiphase rotor, and, in the form of the second portion, the electrical supply power for the payload apparatus. The providing of the mechanical drive power and also of the electrical supply power means in particular that the rotating-field power that can be and/or is provided by the multiphase motor, preferably that can be and/or is produced by the multiphase stator and/or can be and/or is taken up by the multiphase rotor, can be converted at least in part into mechanical drive power and at least in part into electrical supply power. The provided rotating-field power can be divided in particular into the first portion of the rotating-field power and into the second portion of the rotating-field power. The provided rotating-field power acts in particular as a mechanical drive power and in particular simultaneously as an electrical supply power. The first portion corresponds in particular to the mechanical drive power, and the second portion corresponds in particular to the electrical supply power. The input power that can be taken up, or is taken up, at the multiphase stator is typically provided in the rotating-field power that is provided, or can be provided, at the multiphase rotor partly in mechanical work power and partly in electrical supply power. Providing rotating-field power, mechanical drive power or electrical supply power in this manner is fundamentally lossy.

In particular, the rotational movement of the multiphase rotor relative to the multiphase stator can be produced via the mechanical drive power. The production of the rotational movement takes place in particular when the gantry drive is operating as a motor, and comprises in particular increasing the rotational speed in the acceleration stage and/or maintaining the rotational speed after the acceleration stage in the continuation stage. Increasing the rotational speed typically requires more mechanical drive power than maintaining the rotational speed. Maintaining the rotational speed in the continuation stage can comprise a time interval in which the mechanical drive power is equal to zero, and another time interval in which the mechanical drive power is greater than zero. It is conceivable in principle that the rotational speed is reduced and/or the rotational movement is entirely suppressed via the mechanical drive power, something which takes place in particular when the gantry drive is operating as a generator.

A time interval after the acceleration stage can be provided in particular for full-load operation of the payload apparatus. The time interval after the acceleration stage, in particular the continuation stage, can be referred to in particular as the full-load operating stage. Full-load operation of the payload apparatus is defined in particular to mean that during full-load operation of the payload apparatus in the continuation stage, more electrical supply power is consumed than in the acceleration stage. In the full-load operating stage, the electrical supply power can reach a maximum value, for example. After a continuation stage or full-load operating stage, an acceleration stage can take place again. Acceleration stages and continuation stages or full-load operating stages can alternate in particular in a regular manner and/or can occur cyclically.

In the acceleration stage, the electrical supply power is typically greater than zero. In other words, in the acceleration stage, the payload apparatus can be in operation, typically with reduced power. Alternatively or additionally, in the acceleration stage, the electrical supply power can be equal to zero.

The rotating-field power that can be taken in, or is taken in, in particular the electrical supply power that can be provided, or is provided, can appear at an output of the multiphase motor for the payload apparatus. The output of the multiphase motor, in particular the output of a rotating converter or of a stationary converter, can be connected to the payload apparatus. Preferably a DC voltage, or alternatively an AC voltage, exists at the output. Alternatively or additionally, the payload apparatus can form part of the gantry drive. The payload apparatus can be integrated in particular in a circuit arrangement comprising the multiphase motor, in particular the multiphase stator and the multiphase rotor.

In particular, the payload apparatus is not a mechanical drive unit and/or is not suitable for driving the multiphase rotor. In other words, the electrical supply power is in particular not used for the rotational movement of the multiphase rotor. The payload apparatus can be joined to the multiphase stator or to the multiphase rotor for conjoint rotation therewith. The payload apparatus can be electrically connected in such a way that in a circuit arrangement, the multiphase stator is between the multiphase rotor and the payload apparatus, or in such a way that the multiphase rotor is between the multiphase stator and the payload apparatus.

The payload apparatus can provide a parallel and/or series connection of a plurality of electrical payloads. The electrical supply power can be used in particular for a plurality of electrical payloads. An electrical payload can be referred to as an electrical consumer, for example.

It is conceivable that the payload apparatus has a high-voltage generator and/or an X-ray source that can be operated with an electrical supply power greater than 5 kw, in particular greater than 50 kW, preferably greater than 150 kw. The high-voltage generator and/or the X-ray source is typically advantageous for imaging and in operation consumes the electrical supply power. In the X-ray source, electrons are typically accelerated by the high voltage to energies of up to 150 keV. An electron current equals, for example, between 10 and 1000 mA, typically depending on the high voltage or the maximum electrical supply power.

The control unit is designed in particular to control the multiphase motor. The control of the multiphase motor comprises controlling the multiphase stator and/or controlling the multiphase rotor. The control of the multiphase stator comprises in particular controlling the stationary converter. The control of the multiphase rotor comprises in particular controlling the rotating converter.

The control targets of the control are in particular the mechanical drive power and/or the electrical supply power. The control comprises in particular adjusting the apportioning of the rotating-field power between mechanical drive power and electrical supply power. The control comprises in particular impressing a voltage, in particular an amplitude and/or a phase angle, a frequency and/or a slip and/or an output current and/or an output voltage for the payload apparatus, on which the rotating-field power typically depends and/or via which the rotating-field power is controlled. The manipulated variables are thus the voltage, in particular the amplitude and/or the phase angle, the frequency and/or the slip and/or the output current and/or the output voltage. The manipulated variables are usually available to both the multiphase stator and the multiphase rotor. In particular, the control is field-oriented control.

The control unit is typically joined to the multiphase stator. Between the control unit and the multiphase stator can be connected the stationary converter. The stationary converter is fed from, for example, the, preferably three-phase, mains supply, and/or has a three-phase input. It is conceivable in principle that a DC-link circuit containing a rectified mains voltage is provided between the stationary converter and the mains supply. In this case, the stationary converter is preferably also capable of converting, in the manner of an inverter, a DC voltage into an AC voltage, or a stationary inverter is connected in front of the stationary converter. The stationary converter can be in particular what is known as an indirect converter, which typically constitutes a combination of a rectifier and an inverter. The stationary converter has a capacitor, for example.

The control unit is configured in particular to control the multiphase stator, preferably to control the stationary converter and/or the stationary inverter. In particular, the control is the field-oriented control for a type of asynchronous machine. The control of the multiphase stator comprises in particular impressing the voltage, in particular the amplitude and/or the phase angle, and/or the frequency.

The control unit is typically joined to the multiphase rotor. Between the control unit and the multiphase rotor can be connected a rotating converter. The rotating converter is typically fed from the, in particular three-phase, multiphase rotor. The rotating converter can comprise in particular a rotating rectifier, which provides, in particular for the payload apparatus, a DC voltage with the electrical supply power. It is conceivable in principle that a DC-link circuit is provided between the multiphase rotor and the rotating converter. In this case, the rotating converter is preferably also capable of converting, in the manner of an inverter, a DC voltage into an AC voltage, and/or vice versa. In particular, the rotating converter can be a rectifier. The rotating converter has a capacitor, for example.

In this context, the term "stationary" relates only to the arrangement of the one converter on the multiphase stator. In particular, the stationary converter can be called a first converter or stator converter. In this context, the term "rotating" relates only to the arrangement of the other converter on the multiphase rotor. In particular, the rotating converter can be called a further converter or second converter or rotor converter. In principle, the rotating converter and the stationary converter can have the same design or a different design.

The control unit is configured in particular to control the multiphase rotor, preferably to control the rotating converter. In particular, the control is the field-oriented control for a type of asynchronous machine. The control of the multiphase rotor comprises in particular impressing the voltage, in particular the amplitude and/or the phase angle, and/or the frequency.

The direct drive can comprise a sensor unit for measuring the rotational speed of the rotational movement, in particular a mechanical rotational frequency of the multiphase rotor relative to the multiphase stator. The control unit can be connected to the sensor unit for the purpose of receiving a measured value from the sensor unit. The measured value can be time-dependent.

The control unit can vary in particular the first portion by the control of the multiphase stator, and the second portion by the control of the multiphase rotor. The varying comprises in particular an increase or a decrease. The varying of one of the two portions can be performed in such a way that in the case of an increase, the other portion is decreased and/or the rotating-field power is increased, and in the case of a decrease, the other portion is increased and/or the rotating-field power is decreased. For the varying of the first portion and/or the second portion, the control unit alters in particular an operating point of the multiphase stator, in particular of the stationary converter, and/or an operating point of the multiphase rotor, in particular of the rotating converter.

The sum of the first portion and the second portion in particular is less than or equal to 100% of the rotating-field power, in particular less than or equal to 100% of a total power of the rotating-field power. In absolute terms, the total power of the rotating-field power can be altered, in particular up to a maximum value. The maximum value can make use of a power reserve of the gantry drive.

The control unit can comprise a processing unit, in which the field optimized control is modeled by program code means and/or instructions. Alternatively or additionally, the program code means and/or instructions can model the alteration in the operating point of the multiphase stator and/or in the operating point of the multiphase rotor. The principle of how it works is described as follows: the operating point is in particular a function of the multiphase frequency, and defines a torque. The torque/multiphase-frequency characteristic depends on a resistive value of the multiphase rotor, which typically influences the losses in the rotor. The rotating converter emulates the resistive value of the multiphase rotor in particular in the continuation stage or full-load operating stage. The torque typically correlates with the mechanical drive power. The torque can be provided via the rotating-field power. In principle, alternative ways of looking at how it works are conceivable.

The control unit can typically control the operating points at least for the following scenarios:
maximum magnetic flux in order to maximize the mechanical drive power, for instance when a maximum torque is needed in the acceleration stage;
balanced magnetic flux in order to increase the electrical supply power compared with the mechanical drive power. In these two scenarios, the magnetic flux is typically kept constant over time. In other words, these operating points are static. The multiphase motor is not typically operated in saturation. The electrical supply power can be increased in particular by reducing the magnetic flux and hence increasing the slip.

Alternatively or additionally, the control unit can control an operating point for the following scenario:
modulation of the magnetic flux amplitude, in particular when the mechanical drive power is zero and the electrical supply power is greater than zero. In principle, it is conceivable in this scenario that the mechanical drive power is greater than zero. In this scenario, the multiphase motor acts as a transformer, and preferably allows a change in the flux over time.

It is conceivable in principle that the control unit is designed to vary the first portion and/or the second portion by adjusting the slip of the gantry drive. The multiphase frequency f1el of the multiphase stator (stator rotational frequency) minus the multiphase frequency f2el of the multiphase rotor (rotor rotational frequency) typically defines the mechanical rotational frequency fmech of the multiphase rotor:

$fmech=(f1el-f2el)/p$; where $p$ equals the number of pole pairs.

The slip S of the gantry drive, in particular of the multiphase motor, is obtained as follows:

$S=(f1el-fmech \times p)/f1el=f2el/f1el$

Thus adjusting the slip advantageously makes it possible to vary the first portion and/or the second portion. For example, reducing the magnetic flux and/or the stator rotational frequency leads to an increase in the slip. The rotational movement, in particular the mechanical drive power needed therefor, can typically be produced by different combinations of manipulated variables, in particular by a plurality of different combinations of stator rotational frequency and rotor rotational frequency.

The control unit can have an interface for receiving a control signal. The control signal can describe at least one control target and/or one manipulated variable. The control unit is preferably designed to adjust the first portion and/or the second portion according to the control signal. In particular, the control signal can comprise a setpoint value of the first portion and/or of the second portion. The control signal can be time-dependent. The control signal can additionally comprise an actual value of the first portion and/or of the second portion. The control signal can depend on a usage and/or on a user of the gantry drive. The usage can be imaging. The user can be a physician and/or an operator of the gantry drive.

The control signal can comprise at least one value for the acceleration stage and/or one value after the acceleration stage, preferably for the first portion and/or the second portion in each case. The value for the acceleration stage is, for example, the target speed, in particular the speed of rotation of the gantry and/or the mechanical rotational frequency, and/or a drive parameter. The mechanical drive power or torque depends on the target speed. The value after the acceleration stage is in particular a payload apparatus parameter, for example a specified DC-link voltage at the output of the rotating converter. The specified DC-link voltage is usually constant. The payload apparatus parameter can comprise a time for the change into the full-load operating stage or into the acceleration stage, so that the gantry drive can counteract a drop or overshoot in the DC-link voltage by adapting the electrical supply power. The value for, or after, the acceleration stage can be in particular a charging management parameter for an energy buffer. The charging management parameter can be in particular a charging current, a discharging current, a target value for the SoC value. The SoC value typically defines the level of charge of the energy buffer.

The control unit can be connected by wired or wireless mechanism, means and/or device for controlling the multiphase stator and/or the multiphase rotor. In the latter case, in the control path can be provided a wireless transmitter and a wireless receiver, for example, which in particular have an optical, capacitive or inductive design. A wired connection can comprise using a galvanic or resistive control path, for instance in the form of a brush and a slip ring.

An embodiment of the gantry drive provides that the control unit is designed to increase the first portion or the second portion at the expense of the second portion or the first portion respectively. This embodiment is advantageous in particular because it does not require an increase in the rotating-field power. This is advantageous in particular when the rotating-field power cannot be increased because of a lack of power reserves.

Corresponding to the method, according to embodiments of the present invention, an embodiment provides, in an analogous manner to the previous embodiment of the device, that the first portion and/or the second portion are varied via the control unit. Developments of this embodiment relate to the case in which the first portion is adjusted via the control unit in such a way that in the acceleration stage of the multiphase rotor, the first portion is higher compared with the first portion after the acceleration stage, and/or the second portion is adjusted via the control unit in such a way that after the acceleration stage of the multiphase rotor, the second portion is higher compared with the second portion in the acceleration stage.

An embodiment of the gantry drive provides that the control unit is designed to increase the first portion at the expense of the second portion in the acceleration stage of the multiphase rotor. "At the expense of" means in particular that a power delta between the two portions is shifted or reallocated at least substantially by the same amount. In other words, the increase in the first portion by the power delta means that the second portion is simultaneously decreased by the power delta. This embodiment is advantageous in particular because, in the acceleration stage, it is possible to dispense with at least some of the electrical supply power, especially if the payload apparatus is configured for imaging. The imaging is preferably not carried out in the acceleration stage but only after the target speed has been reached, in order to benefit in terms of time from the increased rotational movement.

Corresponding to the method, according to embodiments of the present invention, an embodiment provides, in an analogous manner to the previous embodiment of the device, that in the acceleration stage of the multiphase rotor, the first portion is increased at the expense of the second portion via the control unit.

An embodiment of the gantry drive provides that the control unit is designed to increase the second portion at the expense of the first portion after the acceleration stage of the multiphase rotor. Typically, in the continuation stage, in particular after the target speed has been reached, the payload apparatus needs more electrical supply power, and the multiphase rotor needs less mechanical drive power to maintain the target speed. Hence a further power delta can be shifted to the benefit of the second portion at the expense of the first portion, without having to provide or call upon a power reserve.

Corresponding to the method, according to embodiments of the present invention, an embodiment provides, in an analogous manner to the previous embodiment of the device, that after the acceleration stage of the multiphase rotor, the second portion is increased at the expense of the first portion via the control unit.

An embodiment of the gantry drive provides that the control unit is designed to drive the multiphase motor as a transformer to modulate the magnetic flux in order to vary the first portion and/or the second portion. This embodiment is advantageous in particular when the gantry drive is at a standstill, in order to be able to operate the payload apparatus with the second portion of the rotating-field power.

An embodiment of the gantry drive provides that the control unit is designed to vary the first portion and/or the second portion in accordance with field-oriented control. The field-oriented control comprises in particular subsidiary controls, which model at least one of the manipulated variables in d-coordinates and q-coordinates. The subsidiary controls are in particular machine equations of the multiphase motor in field-oriented coordinates. In field-oriented control, the slip is not typically a direct manipulated variable. It is usually the slip that is altered in the field-oriented control.

Corresponding to the method, according to embodiments of the present invention, an embodiment provides, in an analogous manner to the previous embodiment of the device, that the first portion and/or the second portion are varied in accordance with field-oriented control via the control unit.

An embodiment provides that the gantry drive has an energy buffer, which is electrically connected to the multiphase motor, wherein the control unit is designed to discharge or charge the energy buffer according to the rotating-field power that can be provided. The energy buffer being electrically connected to the multiphase rotor means in particular that the energy buffer and the multiphase rotor jointly form a circuit arrangement or part of a circuit arrangement. In particular, the energy buffer can be part of the gantry drive or of a computed tomography apparatus.

The energy buffer can be electrically connected to the multiphase stator, to the stationary converter, to the multiphase rotor, or to the rotating converter. The energy buffer can be joined to the multiphase stator or to the multiphase rotor for conjoint rotation therewith. The energy buffer on the multiphase stator has the advantage that less mass is rotating and hence a drive power can be lower. Moreover, more installation space is usually available on the multiphase stator than on the multiphase rotor.

The energy buffer on the multiphase rotor has the advantage that the multiphase motor can be smaller or less powerful overall, in particular if the energy buffer is electrically connected to the rotating converter and/or to the multiphase rotor, and/or provides further mechanical drive power and/or electrical supply power. For example, during operation of a payload apparatus that can have peak demands of greater than 5 kW or 50 kW or 150 kW, the rotating-field power can be smaller by at least the factor of 2, 3 or 5 or 10 if the energy buffer is provided at the multiphase rotor for power compensation.

The energy buffer can be a non-rechargeable battery and/or a rechargeable battery and/or a capacitor, in particular a super capacitor, and/or a double-layer capacitor. The energy buffer stores in particular electrical energy. The energy buffer can typically by composed of a plurality of energy buffer cells, which preferably spatially surround the cavity at least partially in the form of a ring. The energy buffer is electrically connected to the multiphase rotor in such a way that the rotating-field power that can be provided can charge the energy buffer. The energy buffer has the advantage that the power reserves of the multiphase motor, in particular of the multiphase rotor and/or of the multiphase stator, can be smaller or completely non-existent. For operating the direct drive under full load and/or peak load, such as in the acceleration stage for instance, the energy buffer can advantageously compensate for at least some of the power reserves. This advantageously allows cost benefits, in particular through savings in material for the multiphase windings. Alternatively or additionally, the installation space close to the cavity is reduced, with the result that the cavity can be bigger.

An embodiment provides that the energy buffer is connected to the multiphase motor, and can be controlled via the control unit in such a way that, in addition to the first portion, a further mechanical drive power for producing the rotational movement of the multiphase rotor can be provided via energy from the energy buffer. The further mechanical drive power in total with the first portion and the second portion typically exceeds the rotating-field power that can be, or is, taken up. In other words, the further mechanical drive power cannot be provided by the rotating-field power at least at one time of operation of the gantry drive. It is conceivable in principle that a total power of the rotating-field power at another time of operation of the gantry drive can equal a total of the further mechanical drive power, the mechanical drive power and the electrical supply power. The providing of the further mechanical drive power typically discharges the energy buffer. This embodiment is advantageous in particular in the acceleration stage, and/or for reducing the power reserves of the multiphase rotor and/or of the multiphase stator.

An embodiment provides that the energy buffer is connected to the multiphase motor, and can be controlled via the control unit in such a way that the energy buffer can be charged when the gantry drive is operating as a generator. In particular, the energy buffer can store the kinetic energy of the multiphase rotor in the form of electrical energy, in which process the energy buffer is charged. The energy buffer can preferably in this way make the multiphase rotor decelerate more sharply. The energy buffer is charged in particular by conversion of the moment of inertia of the rotating multiphase rotor.

An embodiment provides that the energy buffer is connected to the payload apparatus in such a way, and can be controlled via the control unit in such a way, that in addition to the second portion, a further electrical supply power for the payload apparatus can be provided via energy from the energy buffer. The further electrical supply power in total with the first portion and the second portion typically exceeds the rotating-field power that can be, or is, taken up. The providing of the further electrical supply power typically discharges the energy buffer. This embodiment is advantageous in particular after the acceleration stage and/or in the full-load operating stage, and/or for reducing the power reserves of the multiphase motor, in particular of the multiphase rotor and/or of the multiphase stator. An additional advantage to this is that the peak power taken from the mains preferably falls. This typically means that a lower mains supply power is needed. This is advantageous in particular for lower-rated mains supplies provided for operating the gantry drive according to one or more embodiments of the present invention.

An embodiment provides that the energy buffer is connected to the multiphase motor and to the payload apparatus in such a way that the rotating-field power can be provided solely via energy from the energy buffer. In this case, the energy buffer advantageously acts as an uninterruptible power supply. In other words, the gantry drive preferably works without mains supply power when the level of charge of the energy buffer is greater than zero. Such an energy buffer is advantageous in particular, for example, if the mains fails. This embodiment is facilitated in particular by the symmetrical design of the multiphase motor. The control unit is preferably designed to identify the mains failure and to drive the energy buffer accordingly. Looked at in a first way, in this embodiment the further mechanical drive power replaces the first portion, and/or the further electrical supply power replaces the second portion with regard to the usual direction of transmission of the rotating-field power from the multiphase stator to the multiphase rotor. Looked at in a second way, the direction of the rotating-field power is completely reversed, with the result that now the rotating-field power is transmitted from the multiphase rotor to the multiphase stator.

An alternative embodiment provides that the multiphase rotor can be operated solely by the mechanical drive power provided. This embodiment is advantageous in particular because it does not need an energy buffer.

A further alternative embodiment provides that the payload apparatus can be operated solely by the electrical supply power provided. This embodiment is advantageous in particular because it does not need an energy buffer.

The computed tomography apparatus, according to an embodiment of the present invention has:
the gantry drive;
a stationary carrier ring; and
a rotating carrier ring,
wherein the stationary carrier ring is joined to the multiphase stator, and the rotating carrier ring is mounted for conjoint rotation with the multiphase rotor. In other words, the rotating carrier ring rotates jointly with the multiphase rotor relative to the multiphase stator or the stationary carrier ring. The rotating carrier ring and/or the stationary carrier ring can have a central opening for the cavity. An external shape of the stationary carrier ring and/or an external shape of the rotating carrier ring can be in the form of a drum or a disc.

The computed tomography apparatus has the gantry drive, according to one or more embodiments of the present invention, and therefore shares the advantages mentioned above in connection with the gantry drive, and includes the embodiments thereof. The computed tomography apparatus can preferably be lighter because of the reduced installation space, allowing a smaller mechanical drive power to achieve the target speed of the multiphase rotor.

The computed tomography apparatus can comprise a grounding slip ring, which can be provided for regulatory reasons, in particular to ensure safe operation, and/or for operative reasons.

An embodiment provides that the computed tomography apparatus also has an X-ray detector, wherein the electrical supply power can be provided to the X-ray source of the payload apparatus via the rotating-field power. The payload apparatus preferably comprises the X-ray source when preferably the X-ray detector of the computed tomography apparatus is mounted on the rotating carrier ring for conjoint rotation therewith. The X-ray detector and the X-ray source are designed in particular for imaging, and are usually mounted opposite one another on the rotating carrier ring.

The computer program product can be a computer program or comprise a computer program. The computer program product comprises in particular the program code means and/or instructions that model the method steps according to one or more embodiments of the present invention. It is thereby possible to define and repeatedly perform the method according to one or more embodiments of the present invention, and to exercise control over disseminating the method according to one or more embodiments of the present invention. The computer program product is preferably configured such that the processing unit can use the computer program product to perform the method steps according to one or more embodiments of the present invention. The program code means and/or instructions can be loaded in particular into a memory of the processing unit, and typically can be executed by a processor of the processing unit with access to the memory. When the computer program product, in particular the program code means and/or instructions, is executed in the processing unit, typically all the embodiments according to the present invention of the described method can be implemented. The computer program product is stored, for example, on a physical, computer-readable medium and/or digitally as a data packet in a computer network. The computer program product can constitute the physical, computer-readable medium and/or the data packet in the computer network. Hence one or more embodiments of the present invention can also proceed from said physical computer-readable medium and/or from said data packet in the computer network. The physical, computer-readable medium can usually be connected directly to the processing unit, for instance by inserting the physical, computer-readable medium into a DVD drive or by plugging same into a USB port, whereby the processing unit can have access, in particular read access, to the physical, computer-readable medium. The data packet can preferably be retrieved from the computer network. The computer network can comprise the processing unit or be connected directly to the processing unit via a wide area network (WAN) connection and/or via a (wireless) local area network (WLAN or LAN) connection. For instance, the computer program product may be held digitally on a Cloud server at a storage location of the computer network, and be transferred via the WAN via the Internet and/or via the WLAN or LAN to the processing unit, in particular by opening a download link that points to the storage location of the computer program product.

Features, advantages or alternative embodiments mentioned in the description of the device can also be applied to the method, and vice versa, in particular not just in the cases highlighted explicitly above. In other words, claims relating to the method can be developed by features of the device, and vice versa. In particular, the device, according to one or more embodiments of the present invention, can be used in the method.

BRIEF DESCRIPTION OF THE DRAWINGS

The present invention is described and explained in greater detail below with reference to the exemplary embodiments shown in the figures, where the same reference signs are generally used in the following description of the figures to denote structures and units that remain substantially the same as in the first appearance of the structure or unit concerned, and
In which.

DETAILED DESCRIPTION

Figure 1:
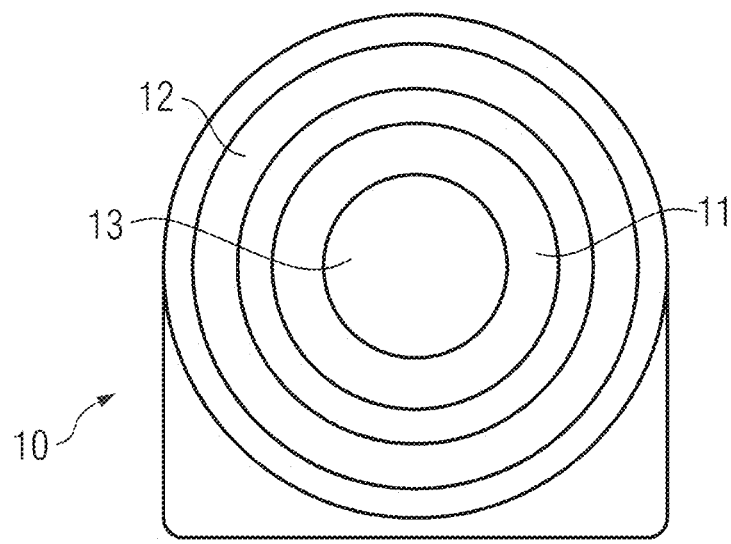
FIG. 1 shows a conventional gantry.

FIG. 1 shows a schematic view of a conventional gantry 10. The conventional gantry 10 has a gantry drive 11 as a mechanical drive for a rotating carrier ring, and in addition a power transmission system 12, which is contact-based in this exemplary embodiment. The contact-based power transmission system 12 is mounted on a rotor, which spatially surrounds a tunnel-shaped cavity 13 for receiving a patient.

Figure 2:
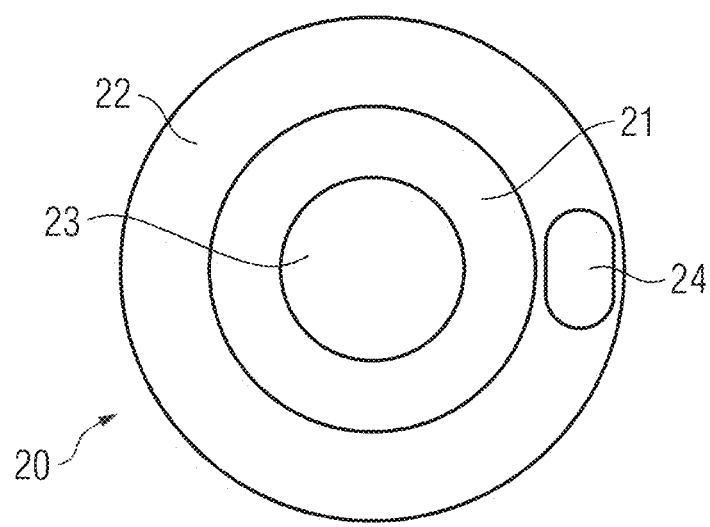
FIG. 2 shows a gantry drive according to embodiments of the present invention.

FIG. 2 shows a schematic view of a gantry drive 20 according to embodiments of the present invention.

The gantry drive 20 has a multiphase stator 21, a multiphase rotor 22, a tunnel-shaped cavity 23 for receiving a patient, and a control unit 24. The multiphase stator 21 and the multiphase motor 22 form a multiphase motor for providing a rotating-field power. A multiphase motor with external rotor is shown. Alternatively, an embodiment of the multiphase motor with internal rotor is conceivable.

The multiphase rotor 22 spatially surrounds the cavity 23. The multiphase stator 21 also spatially surrounds the cavity 23 in this exemplary embodiment. In this exemplary embodiment, the rotating-field power is transmitted substantially in a radial direction, which is usually associated with a drum-shaped embodiment of the multiphase stator 21 and of the multiphase rotor 22. Alternatively, the rotating-field power can be transmitted substantially in an axial direction, in particular the multiphase stator 21 and the multiphase rotor 22 are then disc-shaped.

Via the rotating-field power, in the form of the first portion, can be provided a mechanical drive power for producing a rotational movement of the multiphase rotor 22, and, in the form of a second portion, can be provided an electrical supply power for a payload apparatus 25. The payload apparatus 25 is not shown in FIG. 2. In principle, the payload apparatus 25 can be joined to the multiphase stator 21 or to the multiphase rotor 22 for conjoint rotation therewith.

The control unit 24 is designed to vary the first portion and/or the second portion. FIG. 2 shows the control unit 24 on the rotating part. Alternatively, the control unit 24 can be mounted to be stationary, so that the control unit 24 does not rotate jointly with the multiphase rotor 22.

The control unit 24 is preferably designed to increase the first portion or the second portion at the expense of the second portion or the first portion respectively. The control unit 24 is also preferably designed to increase the first portion at the expense of the second portion in an acceleration stage of the multiphase rotor 22. In addition, the control unit 24 is preferably designed to increase the second portion at the expense of the first portion after the acceleration stage of the multiphase rotor 22. The control unit 24 is preferably designed to vary the first portion and/or the second portion by adjusting the slip of the gantry drive 20. Alternatively or additionally, the control unit 24 is designed to drive the multiphase motor as a transformer to modulate the magnetic flux in order to vary the first portion and/or the second portion.

Figure 3:
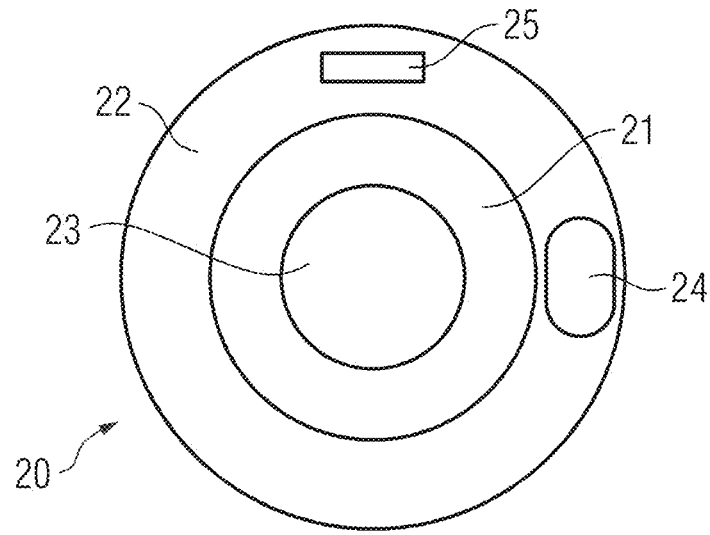
FIG. 3 shows the gantry drive in a first exemplary embodiment.

FIG. 3 shows the gantry drive 20 of FIG. 2 in a first exemplary embodiment. In this exemplary embodiment, the payload apparatus 25 is mounted on the multiphase rotor 22 for conjoint rotation therewith.

In particular, the payload apparatus 25 has a high-voltage generator and/or an X-ray source. This or these can preferably be operated with an electrical supply power of greater than 5 kW, in particular greater than 50 kW, particularly advantageously greater than 150 kW, which can be provided by the gantry drive 20.

Figure 4:
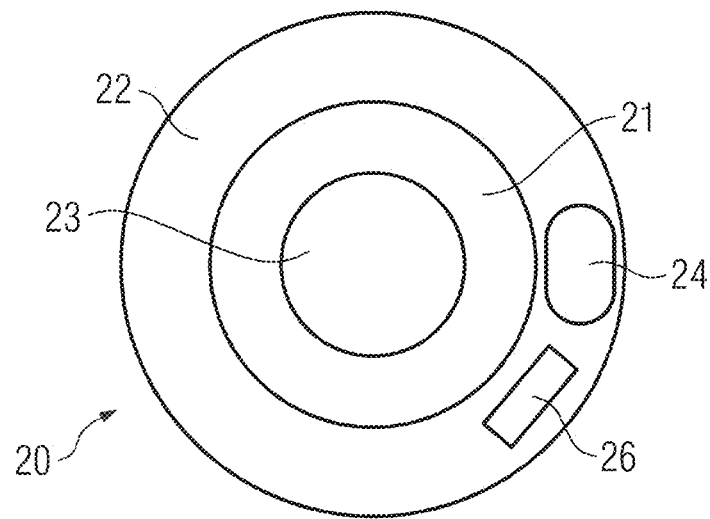
FIG. 4 shows the gantry drive in a second exemplary embodiment.

FIG. 4 shows the gantry drive 20 of FIG. 2 in a second exemplary embodiment.

The gantry drive 20 has an energy buffer 26, which is electrically connected to the multiphase motor and joined to the multiphase rotor 22 for conjoint rotation therewith. Alternatively, the energy buffer 26 can be joined to the multiphase stator 21 for conjoint rotation therewith. The control unit 24 is designed to discharge or charge the energy buffer 26 according to the rotating-field power that can be provided.

The energy buffer 26 is preferably connected to the multiphase motor, and can be controlled via the control unit 24 in such a way that in addition to the first portion, a further mechanical drive power for producing the rotational movement of the multiphase rotor 22 can be provided via energy from the energy buffer 26. Alternatively or additionally, the energy buffer 26 is connected to the multiphase motor, and can be controlled via the control unit 24 in such a way that the energy buffer 26 can be charged when the gantry drive 20 is operating as a generator. The energy buffer 26 is advantageously connected to the payload apparatus 25 in such a way, and can be controlled via the control unit 24 in such a way, that in addition to the second portion, a further electrical supply power for the payload apparatus 25 can be provided via energy from the energy buffer 26. Alternatively or additionally, the energy buffer 26 is connected to the multiphase motor and to the payload apparatus 25 in such a way that the rotating-field power can be provided solely via energy from the energy buffer 26.

Figure 5:
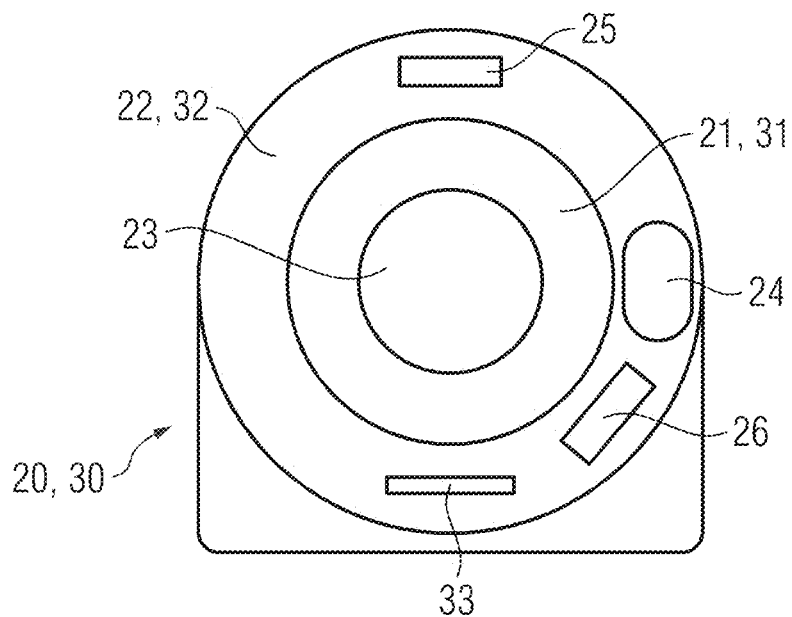
FIG. 5 shows a computed tomography apparatus according to embodiments of the present invention.

FIG. 5 shows a schematic view of a computed tomography apparatus 30 according to embodiments of the present invention.

The computed tomography apparatus 30 has the gantry drive 20, a stationary carrier ring 31, and a rotating carrier ring 32. The stationary carrier ring 31 is joined to the multiphase stator 21. The rotating carrier ring 32 is mounted for conjoint rotation with the multiphase rotor 22.

The stationary carrier ring 31 and/or the rotating carrier ring 32 can be made of metal, for example aluminum, or a plastic. In an embodiment made of metal, the stationary carrier ring and/or the rotating carrier ring can be provided as an electrical ground connection. It is conceivable to reinforce the plastic with additional, in particular metallic, inserts or structures. An external shape of the stationary carrier ring 31 and/or of the rotating carrier ring 32 can be drum-shaped or disc-shaped.

The stationary carrier ring 31 is typically joined to the multiphase stator 31 for conjoint rotation therewith. The rotating carrier ring 32 is typically joined to the multiphase rotor 32 for conjoint rotation therewith. The stationary carrier ring 31 can typically be fixed to, or on, a floor via a base.

The computed tomography apparatus 30 preferably has an X-ray detector 33. The electrical supply power can advantageously be provided to an X-ray source of the payload apparatus 25 via the rotating-field power. Alternatively or additionally, the electrical supply power can be provided to the X-ray detector 33 via the rotating-field power.

Figure 6:
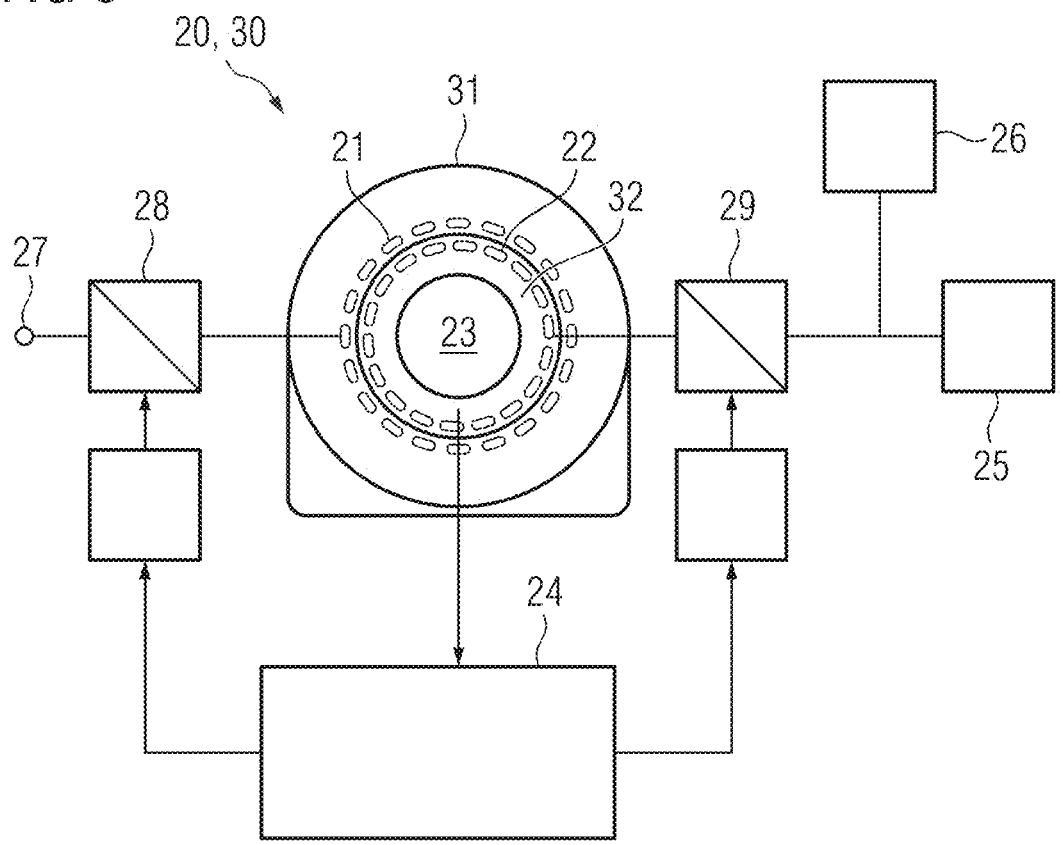
FIG. 6 shows the computed tomography apparatus in a first exemplary embodiment.

FIG. 6 shows a schematic control circuit of the computed tomography apparatus 30 in a first exemplary embodiment. Unlike the previous exemplary embodiment, the multiphase rotor 22 is an internal rotor in this exemplary embodiment. The multiphase windings of the multiphase stator 21, and the multiphase windings of the multiphase rotor 22 are shown as elliptical units, which are mounted in the form of a ring around the cavity 23. The number of multiphase windings shown serves only for illustrative purposes.

The control unit 24 controls a stationary converter 28 and a rotating converter 29 according to a mechanical rotational frequency of the multiphase rotor 22. The control of the stationary converter 28 and of the rotating converter 29 is performed in particular by adjusting a manipulated variable, preferably by impressing a voltage, in particular an amplitude and/or a phase angle, a frequency and/or a slip and/or an output current and/or an output voltage for the payload apparatus 25.

Figure 7:
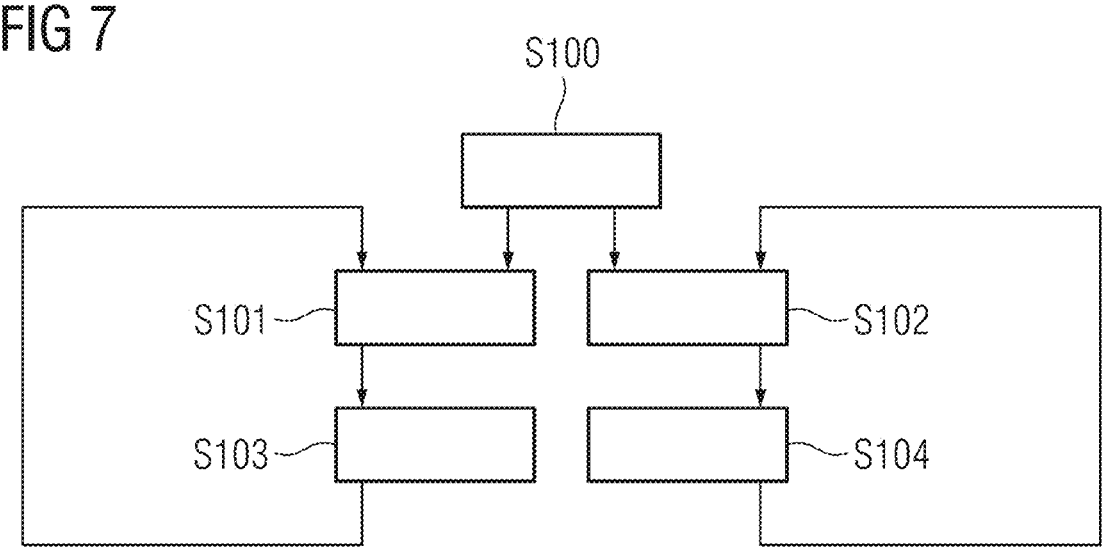
FIG. 7 shows a method according to embodiments of the present invention.

FIG. 7 shows a method, according to embodiments of the present invention, for producing a rotational movement of a multiphase rotor 22 via a gantry drive 20 in a flow diagram having the method steps S100 to S102:

Method step S100 denotes providing a rotating-field power in a multiphase motor.

Method step S101 denotes that a first portion of the rotating-field power acts as a mechanical drive power for producing the rotational movement of the multiphase rotor 22 of the multiphase motor.

Method step S102 denotes that a second portion of the rotating-field power acts as an electrical supply power for the payload apparatus 25.

FIG. 7 also shows possible developments having the method steps S103 and S104:

The optional method step S103 denotes that via a control unit 24, the first portion is adjusted in such a way that in an acceleration stage of the multiphase rotor 22, the first portion is higher compared with the first portion after the acceleration stage.

The optional method step S104 denotes that via a control unit 24, the second portion is adjusted in such a way that after an acceleration stage of the multiphase rotor 22, the second portion is higher compared with the second portion in the acceleration stage.

Figure 8:
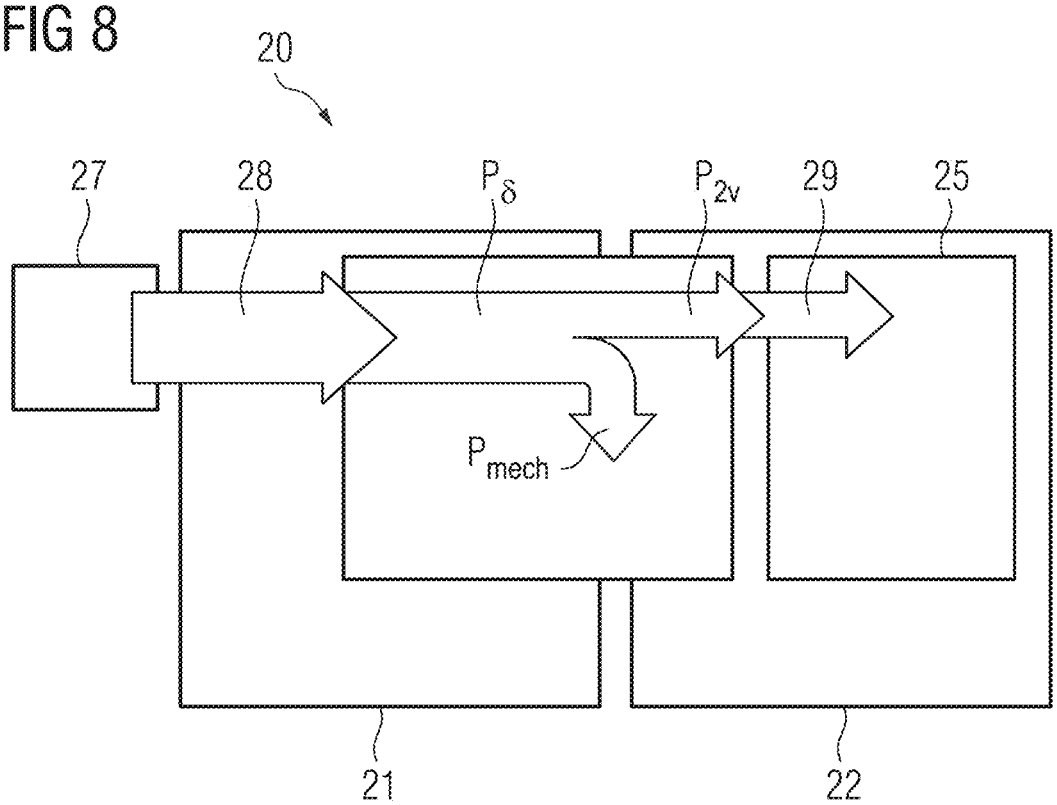
FIG. 8 shows a power flow in the gantry drive for a first operating mode.

FIG. 8 shows in a flow diagram the flow of the powers in the gantry drive 20, according to embodiments of the present invention, for a first operating mode.

In particular, the multiphase stator 21 provides the rotating-field power Pδ across the air gap, which is split into the first portion, the mechanical drive power Pmech, and into the second portion, the electrical supply power P2v. At the three-phase mains supply 27 having an input power is connected a stationary converter 28. From the input power is produced the rotating-field power Pδ, which provides both the mechanical drive power Pmech for producing the rotational movement of the multiphase rotor 22 and the electrical supply power P2v for the payload apparatus 25.

Figure 9:
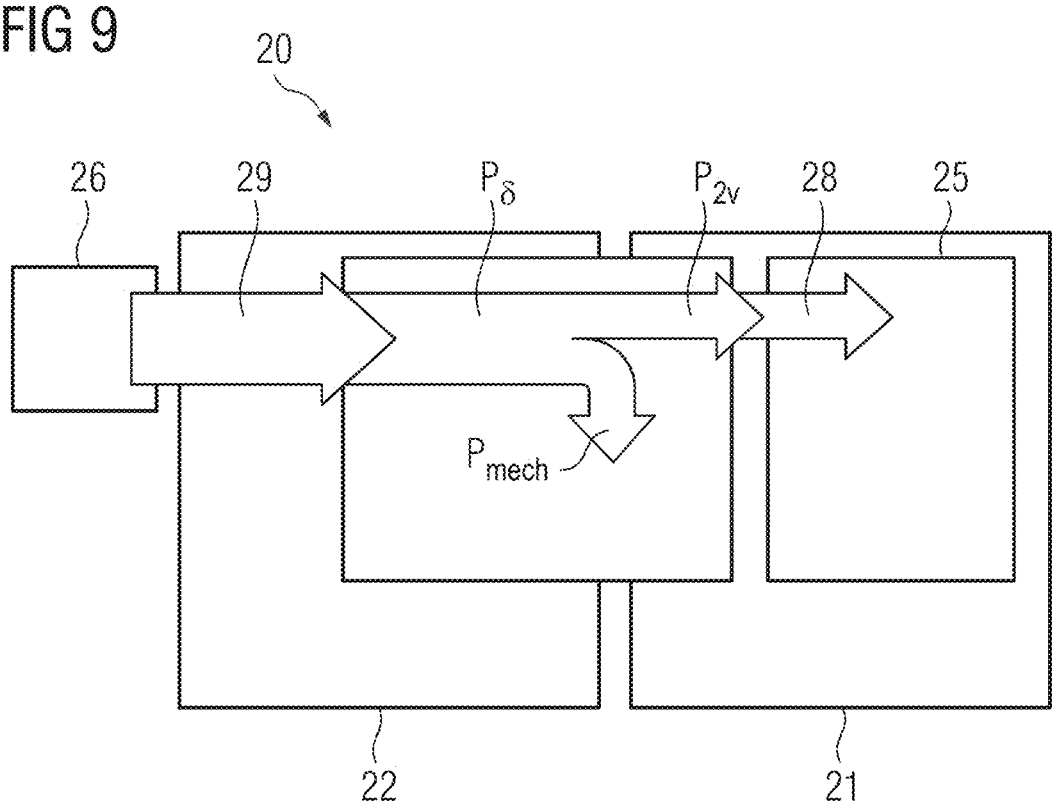
FIG. 9 shows a power flow in the gantry drive for a second operating mode.

FIG. 9 shows in a flow diagram the flow of the powers in the gantry drive 20 for a second operating mode. Unlike the exemplary embodiment shown in FIG. 8, the direction of the rotating-field power is completely reversed as an explanatory model, with the result that now the rotating-field power is transmitted from the multiphase rotor 22 to the multiphase stator 21. Furthermore, in this exemplary embodiment, the payload apparatus 25 is provided on the stator side, whereas the payload apparatus in FIG. 8 is provided on the rotor side.

The gantry drive 20 has the energy buffer 26, which is electrically connected to the multiphase motor. The energy buffer 26 is connected to the multiphase motor and to the payload apparatus 25 in such a way that the rotating-field power can be provided solely via energy from the energy buffer 26.

Figure 10:
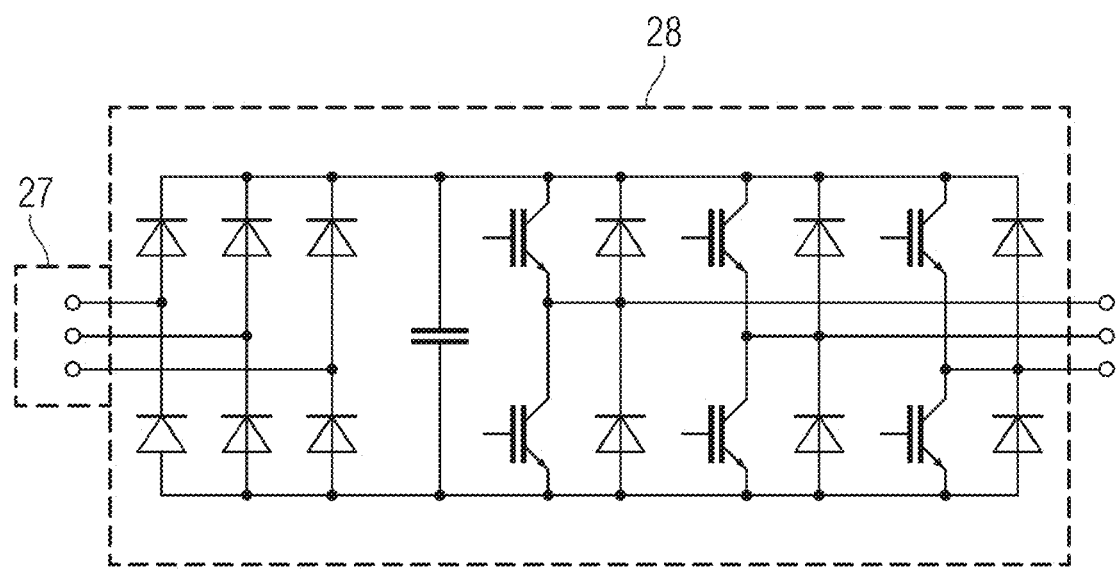
FIG. 10 shows a stationary converter.

FIG. 10 shows a circuit arrangement of the stationary converter 28.

Figure 11:
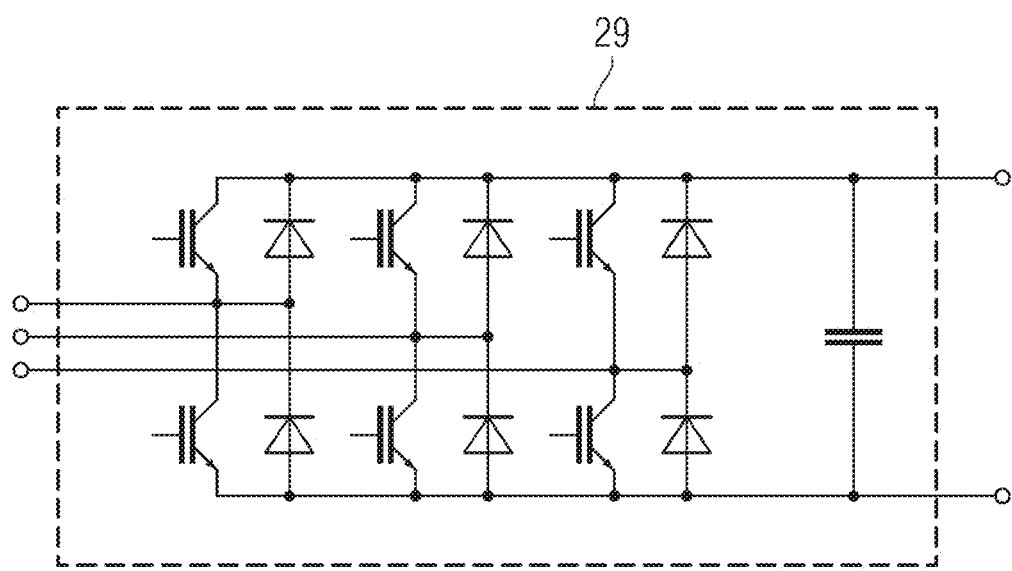
FIG. 11 shows a rotating converter.

FIG. 11 shows a circuit arrangement of the rotating converter 29. The symmetry of the multiphase motor is evident in the circuit arrangements shown in FIG. 10 and FIG. 11.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents. Although the present invention has been illustrated and described in detail using the preferred exemplary embodiments, the present invention is not limited by the disclosed examples, and a person skilled in the art can derive other variations therefrom that are still covered by the scope of protection of the present invention.

What is claimed is:

1. A gantry drive comprising:
a multiphase stator;
a multiphase rotor;
a tunnel-shaped cavity configured to receive a patient; and
a controller
wherein the multiphase rotor spatially surrounds the tunnel-shaped cavity,
wherein the multiphase stator and the multiphase rotor form a multiphase motor configured to provide a rotating-field power,
wherein, a first portion of the rotating-field power provides a mechanical drive power to produce a rotational movement of the multiphase rotor, and a second portion of the rotating-field power provides an electrical supply power for a payload apparatus, and
wherein the controller is configured to vary at least one of the first portion or the second portion.

2. The gantry drive as claimed in claim 1, wherein the controller is configured to increase the first portion or the second portion at the expense of the second portion or the first portion, respectively.

3. The gantry drive as claimed in claim 2, wherein the controller is configured to at least one of
increase the first portion at the expense of the second portion in an acceleration stage of the multiphase rotor, or
increase the second portion at the expense of the first portion after the acceleration stage of the multiphase rotor.

4. The gantry drive as claimed in claim 3, wherein the controller is configured to drive the multiphase motor as a transformer to modulate a magnetic flux to vary at least one of the first portion or the second portion.

5. The gantry drive as claimed in claim 3, wherein the controller is configured to vary at least one of the first portion or the second portion in accordance with a field-oriented control.

6. The gantry drive as claimed in claim 1, wherein the controller is configured to drive the multiphase motor as a transformer to modulate a magnetic flux to vary at least one of the first portion or the second portion.

7. The gantry drive as claimed in claim 1, wherein the controller is configured to vary at least one of the first portion or the second portion in accordance with a field-oriented control.

8. The gantry drive as claimed in claim 1, further comprising:
an energy buffer electrically connected to the multiphase motor, and wherein
the controller is configured to discharge or charge the energy buffer according to the rotating-field power.

9. The gantry drive as claimed in claim 8, wherein the energy buffer is configured to be controlled by the controller such that, in addition to the first portion, a further mechanical drive power to produce the rotational movement of the multiphase rotor is provided via energy from the energy buffer.

10. The gantry drive as claimed in claim 9, wherein the energy buffer is configured to be controlled by the controller such that the energy buffer is chargeable when the gantry drive is operating as a generator.

11. The gantry drive as claimed in claim 9, wherein the energy buffer is connected to the payload apparatus and configured to be controlled by the controller such that, in addition to the second portion, a further electrical supply power for the payload apparatus is provided via energy from the energy buffer.

12. The gantry drive as claimed in claim 8, wherein the energy buffer is configured to be controlled by the controller such that the energy buffer is chargeable when the gantry drive is operating as a generator.

13. The gantry drive as claimed in claim 8, wherein the energy buffer is connected to the payload apparatus and configured to be controlled by the controller such that, in addition to the second portion, a further electrical supply power for the payload apparatus is provided via energy from the energy buffer.

14. The gantry drive as claimed in claim 8, wherein the energy buffer is connected to the payload apparatus such that the rotating-field power is provided solely via energy from the energy buffer.

15. A computed tomography apparatus comprising:
the gantry drive as claimed in claim 1;
a stationary carrier ring; and
a rotating carrier ring,
wherein the stationary carrier ring is joined to the multiphase stator, and
wherein the rotating carrier ring is mounted for conjoint rotation with the multiphase rotor.

16. The computed tomography apparatus as claimed in claim 15, further comprising:
an X-ray detector, wherein
the electrical supply power is provided to an X-ray source of the payload apparatus via the rotating-field power.

17. A method for producing rotational movement of a multiphase rotor via the gantry drive as claimed in claim 1, the method comprising:
providing the rotating-field power in the multiphase motor such that the first portion of the rotating-field power acts as a mechanical drive power for producing the rotational movement of the multiphase rotor of the multiphase motor, and such that the second portion of the rotating-field power acts as the electrical supply power for the payload apparatus.

18. The method as claimed in claim 17, further comprising:
adjusting, via the controller, the first portion such that in an acceleration stage of the multiphase rotor, the first portion is higher compared with the first portion after the acceleration stage.

19. The method as claimed in claim 17, further comprising:
adjusting, via the controller, the second portion such that, after an acceleration stage of the multiphase rotor, the second portion is higher compared with the second portion in the acceleration stage.

20. A non-transitory computer-readable storage medium storing computer-executable instructions that, when executed by at least one processor of a gantry drive, cause the gantry drive to perform a method as claimed in claim 17.

* * * * *